United States Patent [19]

Anderson et al.

[11] Patent Number: 5,476,966
[45] Date of Patent: Dec. 19, 1995

[54] METHOD FOR DEPLETION OF GLUTATHIONE

[75] Inventors: Mary Anderson; Alton Meister, both of New York, N.Y.

[73] Assignee: Cornell Research Foundation, Inc., Ithaca, N.Y.

[21] Appl. No.: 372,873

[22] Filed: Jan. 13, 1995

Related U.S. Application Data

[63] Continuation of Ser. No. 154,725, Nov. 19, 1993, abandoned, which is a continuation of Ser. No. 990,944, Dec. 14, 1992, abandoned, which is a continuation of Ser. No. 858,424, Mar. 24, 1992, abandoned, which is a continuation of Ser. No. 512,614, Apr. 11, 1990, abandoned, which is a continuation of Ser. No. 170,511, Mar. 21, 1988, abandoned.

[51] Int. Cl.$^6$ ..................... C07C 61/08
[52] U.S. Cl. ............. 562/507; 560/13; 560/125; 560/149; 560/150; 562/430
[58] Field of Search ............. 560/13, 125, 149, 560/150; 562/556, 430, 507; 514/562, 529, 538, 550

[56] References Cited

FOREIGN PATENT DOCUMENTS

| 62-126163 | 6/1987 | Japan . |
| 0126163 | 6/1987 | Japan ........................ 562/556 |

OTHER PUBLICATIONS

Griffith, J. Biol. Chem., 254, pp. 7558–7560 (1979).
Meister, Current Topics in Cellular Regulation, 26, pp. 383–394 (1985).
Seelig, Methods in Enzymology, 113, pp. 379–390 (1985).
1988 FASEB Abstract.
Griffith et al, J. Biological Chem., 1979, 254:1205–1210.
Meister et al, Cancer Treat. Reports, 1979, 63:1115–1121.
Griffith, J. Biological Chem., 1982, 257:13704–13712.
Dethmers et al, Proc. Nat'l Acad. Sci. USA, 1981, 78:7492–7496.
Meister, Science, 1983, 220:472–477.
Meister, Hepatology, 1984, 4:739–742.
Griffith et al, Proc. Nat'l Acad. Sci. USA, 1985, 82:4668–4672.
Meister, Nutritional Rev., 1984, 42:397–410.
Anderson, Methods in Enzymology, 1985, 113:548–555.

*Primary Examiner*—Michael L. Shippen

[57] ABSTRACT

This invention relates to certain S-substituted homocysteine sulfoximines and their uses. Buthionine sulfoximine (BSO) appears to have significant uses for chemotherapy and radio therapy, especially combination chemotherapy and radiation therapy and for treatment of subjects with parasitic infections. The compounds of the invention have the same above-mentioned utilities as BSO but have one or more superior attributes when compared to BSO.

2 Claims, 1 Drawing Sheet

METHOD FOR DEPLETION OF GLUTATHIONE

This invention was made with Government support from the National Institutes of Health (United States Public Health Service). The Government has certain rights to this invention. This application is a continuation of application Ser. No. 08/154,725, filed Nov. 19, 1993, now abandoned, which is a continuation of application Ser. No. 07/990,944, filed Dec. 14, 1992, now abandoned, which is a continuation of Ser. No. 07/858,424, filed Mar. 24, 1992, now abandoned, which is a continuation of application Ser. No. 07/512,614, filed Apr. 11, 1990, now abandoned, which is a continuation of Ser. No. 07/170,511, filed Mar. 21, 1988, now abandoned.

FIELD OF THE INVENTION

The present invention relates to a method for decreasing glutathione levels in cells and tissues. More specifically the invention relates to the administration of certain S-(hydrocarbyl)homocysteine sulfoximines to a subject so as to decrease glutathione levels, which is useful for chemo- and radio-treatment of tumors and parasites as well as for increasing the toxicity of drugs and pesticides.

BACKGROUND OF THE INVENTION

Studies on the metabolism of glutathione indicate several functions of glutathione, which include catalysis, metabolism, transport and cellular protection against reactive oxygen compounds, toxic compounds, and free radicals (see FIG. 1). Glutathione is synthesized intracellularly by the consecutive actions of γ-glutamylcysteine and glutathione synthetases. Transport (export) of glutathione is characteristic of many cells and is of great importance in protection of cell membranes. Intracellular glutathione disulfide is a substrate of glutathione reductase (which uses reduced pyridine nucleotide) to provide cells with a reducing environment; thus under normal conditions less than 1% of total cellular glutathione is glutathione disulfide and little glutathione exists as mixed disulfides with proteins or low molecular weight thiols. Glutathione peroxidase catalyses the glutathione-dependent reduction of hydrogen peroxide and of other peroxides which are cytotoxic. Certain glutathione S-transferase catalyze the reduction of lipid peroxides; glutathione reduces the oxy radical form of α-tocopherol which is also involved in cell membrane protection. Free radicals are destroyed by glutathione in an apparently nonenzymatic reaction.

Glutathione is a specific cofactor for several enzymes such as glyoxalase, maleylacetoacetate isomerase, formaldehyde dehydrogenase, dehydrochlorinases, and prostaglandin endoperoxidase isomerases.

Glutathione reacts enzymatically (glutathione S-transferases) and nonenzymatically to form glutathione S-conjugates with endogenous compounds (e.g., leukotriene A, estrogens, prostaglandins) and exogenous compounds (e.g., bromobenzene, melphalan, etc.). These glutathione S-conjugates are metabolized via the mercapturic acid pathway. This pathway is a route of drug detoxication.

Depletion of cellular glutathione by inhibitors of γ-glutamylcysteine synthetase should make tumor cells more susceptible to many anti-cancer drugs and to radiation. By depleting glutathione levels the destructive effects of reactive oxygen intermediates and of free radicals is used to advantage. Most normal cells have a large excess of glutathione, but tumor cells and parasites may have levels of glutathione that are close to that required for survival. Thus depletion of glutathione leads to selective sensitization of cells under hypoxic conditions (thereby decreasing the oxygen enhancement ratio). Certain tumor cells that have become resistant to drugs such as phenylalanine mustard, develop higher glutathione levels than the sensitive cells. Treatment of the resistant cells with the γ-glutamylcysteine synthetase inhibitor, buthionine sulfoximine, depletes glutathione levels and leads to a reversal of drug resistance. In studies on human ovarian tumors, it was found that resistance to one drug led to a cross resistance to other anti-cancer drugs and radiation; thus increased glutathione levels seems to be a factor in cellular resistance.

It was recognized that depletion of cellular glutathione by treatment with the sulfoximine inhibitors of γ-glutamylcysteine synthetase might make tumor cells more susceptible to the effects of radiation and of certain chemotherapeutic agents Meister et al, *Cancer Treat. Rep.*, 1979, 63:1115–1121. In this approach, the destructive effects of reactive oxygen intermediates, such as hydrogen peroxide and free radicals are used advantageously. Glutathione functions to protect cells against toxic compounds of both endogenous and exogenous origin. It destroys reactive oxygen compounds and free radicals, and forms conjugates with certain compounds that have electronegative moieties. That cells depleted of glutathione become more sensitive to radiation and to the effects of certain toxic compounds is in accord with these conclusions.

In studies on three human lymphoid cell lines, the cells were depleted of glutathione to about 5% of the control levels by incubation in media containing buthionine sulfoximine. The glutathione levels of the cells decrease progressively over a period of 50 hours. Although cells with a level of 0.09 mM glutathione (4% of controls) were 85% viable, further decrease in glutathione level was associated with marked loss of viability. Cells that had 4–5% of the control levels of glutathione were much more sensitive than were control cells to the effects of γ-radiation. About 50% of the intracellular glutathione that disappeared from cells of the CEM line was found in the medium. Although the medium was supplemented with L-serine plus borate to inhibit cellular γ-glutamyl transpeptidase activity, such inhibition was incomplete so that less than theoretical recovery of the exported glutathione was found. The rate at which cellular glutathione is depleted is determined by the rate of glutathione export. Cells that export glutathione very slowly exhibit a very slow decline in cellular glutathione level when treated with buthionine sulfoximine. Depletion of cellular glutathione of human lymphoid cells to about 5% of the control levels led to a marked increase in sensitivity to radiation. Similar results have been obtained on cultured human lung carcinoma and on other tumor cells Biaglow et al, *Radiat. Res.*, 1983, 95:437; Mitchell, et al, *Radiat. Res.*, 1983, 96:422. Suspension of V79 cells in media containing buthionine sulfoximine led to selective e sensitization to radiation under hypoxic conditions and to a decrease of the oxygen enhancement ratio Biaglow et al, *Radiat. Res.*, 1983, 95:437; Guichard et al, *Proc. Radiat. Res. Soc.*, 1983, Abstr. Dc10. A considerable literature has developed on the sensitization of various types of cells, especially tumor cells, to radiation and to drugs by use of buthionine sulfoximine to deplete cellular glutathione (see, for example Midander et al, *Radiosensitization Newsletter*, 1984, 3(1):1–2; Biaglow et al, *Radiat. Res*, 1983, 95:437; Mitchell et al, *Radiat. Res.*, 1983, 96:422; Guichard et al, *Proc. Radiat. Res. Soc.*, 1983, Abstr. Dc10; Russo et al, *Int. J. Radiat. Oncol. Biol Phys.*, 1986, 12–1347–1354; Shrieve et al, *Radiat. Res.*, 1985, 102:283–294; Yu et al, *Int. J. Radiat. Onol. Biol. Phys.*, 1984, 10:1265–1269; Clark et al, *Int. J. Radiat. Oncol. Biol. Phys.*, 1986, 12:1121–1126; Arrick et al, *J. Biol. Chem.*, 1982, 257:1231; Russo et al, *Cancer Treat. Rep.*, 1985, 69:1293–1296. Most of thee studies were carried out on cultured cells or cell suspensions. Studies on mice bearing $B_{16}$ melanomas have also shown that treatment of the animals with buthionine sulfoximine sensitizes the tumors to radiation. In these studies, the tumors were implanted in the footpads of mice and allowed to grow to a size of 250 mm$^3$. The mice were given buthionine sulfoximine and were irradiated when the glutathione content of the tumors was about 20% of that of untreated controls. A significant decrease in tumor size and a significant increase in longevity was found.

Studies on mice depleted of glutathione by administration of buthionine sulfoximine led to increased sensitivity (a decrease of about 80% in the $LD_{50}$ value) to acetaminophen. Studies on the oxidative cytolysis of several tumor cell lines by glucose oxidase, and by activated macrophages and granulocytes in the presence of phorbol myristate acetate, showed that depletion of glutathione by incubation in medium containing buthionine sulfoximine enhanced the degree of cytolysis Arrick et al *J. Biol. Chem.*, 1982, 257:1231. The recovery of tumor cell resistance to peroxide was closely correlated with the resynthesis of cellular glutathione. Glutathione depletion sensitizes certain tumors to the effects of sulfhydryl reactive drugs Arrick et al, *J. Clin. Invest.*, 1983, 71:258.

In a study in which six mice infected with *Trypanosoma brucei* were treated with buthionine sulfoximine, two mice were apparently cured and four mice survived significantly longer than did untreated infected controls Arrick et al, *J. Exp. Med.*, 1981, 153:720. This organism apparently does not contain catalase and the findings therefore suggest that depletion of glutathione can be an effective approach for the destruction of cells that lack catalase; thus, the glutathione peroxidase system is the only available mechanism for destruction of hydrogen peroxide.

In early studies on the effects of certain antineoplastic agents, it was observed that tumors developed increased levels of thiols. Vistica and collaborators examined the toxicity of phenylalanine mustard toward resistant and sensitive mouse L1210 leukemia cells. The dose of phenylalanine mustard needed to kill the most resistant cells was substantially higher than that required to kill the most sensitive cell lines. It was shown that the resistance to phenylalanine mustard was not related to differences in uptake or efflux of the drug, but rather to the cellular level of glutathione. It was also observed that the resistant cells converted phenylalanine mustard to a non-toxic hydroxy derivative in a glutathione-dependent dehydrochlorination reaction. [Presumably this is similar to that found in houseflies that have developed resistance to the insecticide DDT (1,1,1-trichloro-2,2-bis(p-chlorophenyl)ethane)]. Treatment of the resistant cells with buthionine sulfoximine led to resensitization of the tumor cells to phenylalanine mustard. In studies on mice bearing resistant tumors, sensitization of the tumors to the effects of phenylalanine mustard was achieved by continuous intraperitoneal infusion of buthionine sulfoximine; and increase in the life span of these animals was observed. It was also found that phenylalanine mustard-resistant cells were able to convert more of the mustard to its nontoxic hydroxy derivative than were the mustard-sensitive cells.

Human ovarian cancer cells that are resistant to phenylalanine mustard also exhibit increased levels of glutathione Green et al, *Cancer Res.*, 1984, 44:5427–5431; Behrens et al, *Proc. Amer. Assoc. Can. Res.*, 1984, 35:336; Hamilton et al, *Cancer Res.*, 44:5286–5290; Louie et al, *Biochem. Pharmacol.*, 1985, in press; Hamilton et al, *Biochem. Pharmacol.*, 1985, 34:2583–2586; Ozols et al, "Glutathione Depletion with Buthionine Sulfoximine: Potential Clinical Applications" in Biochemical Modulators: Experimental and Clinical Approaches; Valeriote et al, Eds.; Martinus Nijhaus: Boston, 1986, pp. 277–294.

Reversal of resistance can be achieved in such cells by depletion of glutathione by use of buthionine sulfoximine. It is of interest that resistance of these tumors to phenylalanine mustard was accompanied by resistance to other drugs such as adriamycin; in addition, the phenylalanine mustard-resistant cells are also resistant to radiation. Glutathione depletion significantly increases the sensitivity of the resistant cells to the drugs and to radiation. The common denominator that underlies such resistance is increased cellular levels of glutathione. It should be mentioned, however, that there is evidence that other factors play a role in resistance and that some types of resistance to drugs are not associated with elevation of glutathione levels. The effects observed on phenylalanine-mustard resistant human ovarian tumor cells grown in nude mice, i.e., reversal of resistance after treatment with buthionine sulfoximine, have led to consideration of the use of buthionine sulfoximine in the therapy of humans with ovarian tumors; Ozols et al, supra.

The collected data indicate that depletion of glutathione by administration of buthionine sulfoximine may be useful in cancer chemotherapy and in radiation therapy of cancer Arrick et al, *Cancer Res.*, 1984, 44:4224–4232. Depletion is effective when the tumor cells and normal cells have significantly different requirements for glutathione. Many normal cells probably have an excess of glutathione whereas certain tumors and parasites contain levels of glutathione that are close to the minimal required for survival. The response of some cells to anticancer agents and other toxic compounds (see, for example Lipke et al, *J. Biol. Chem.*, 1959, 254:2131–2128; Goodchild et al, *Biochem. J.*, 1970, 117:1004–1009; Balabaskaran et al, *Biochem. J.*, 1970, 117:989–996; Dinamarca et al, *Arch. Biochem. Biophys.* 1971, 147:374–383) leads to increased levels of glutathione (probably due to induction of the synthetases), which are responsible for one type of drug resistance. As one would expect, development of resistance associated with elevated glutathione levels to one drug would lead to resistance to others and to radiation.

Tumors with low levels of catalase and which therefore depend upon the activities of glutathione peroxidase and of glutathione S-transferases for destruction of peroxides, would be expected to become less viable during glutathione depletion. Depletion of glutathione in a tumor cell that lacks catalase altogether would be expected to lead to death of the cell, but normal cells, which have catalase, might not be significantly affected. Tumors relatively resistant to radiation and that have high levels of glutathione would be expected to become more sensitive to radiation after cellular levels of glutathione are decreased.

The following references inter alia describe buthionine sulfoximine and related compounds and their uses. These compounds and their described uses appear to be relevant prior art:

Griffith et al, *J. Biological Chem.*, 1979, 254:1205–1210;
Griffith et al, *J. Biological Chem.*, 1979, 254:7558–7560;
Meister et al, *Cancer Treat. Reports.*, 1979, 63.:1115–1121;

Griffith, *J. Biological Chem.*, 1982, 257:13704–13712;
Dethmers et al, *Proc. Nat'l. Acad. Sci. USA*, 1981, 78:7492–7496;
Meister, *Science*, 1983, 220:472–477;
Meister, *Hepatology*, 1984, 4:739–742;
Meister, *Nutritional Rev.*, 1984, 42:397–410;
Meister, *Current Topics in Cellular Regulation*, 1985, 26:383–394;
Griffith et al, *Proc. Nat'l Acad. Sci. USA*, 1985, 82:4668–4672.

DESCRIPTION OF THE INVENTION

Figure 1:
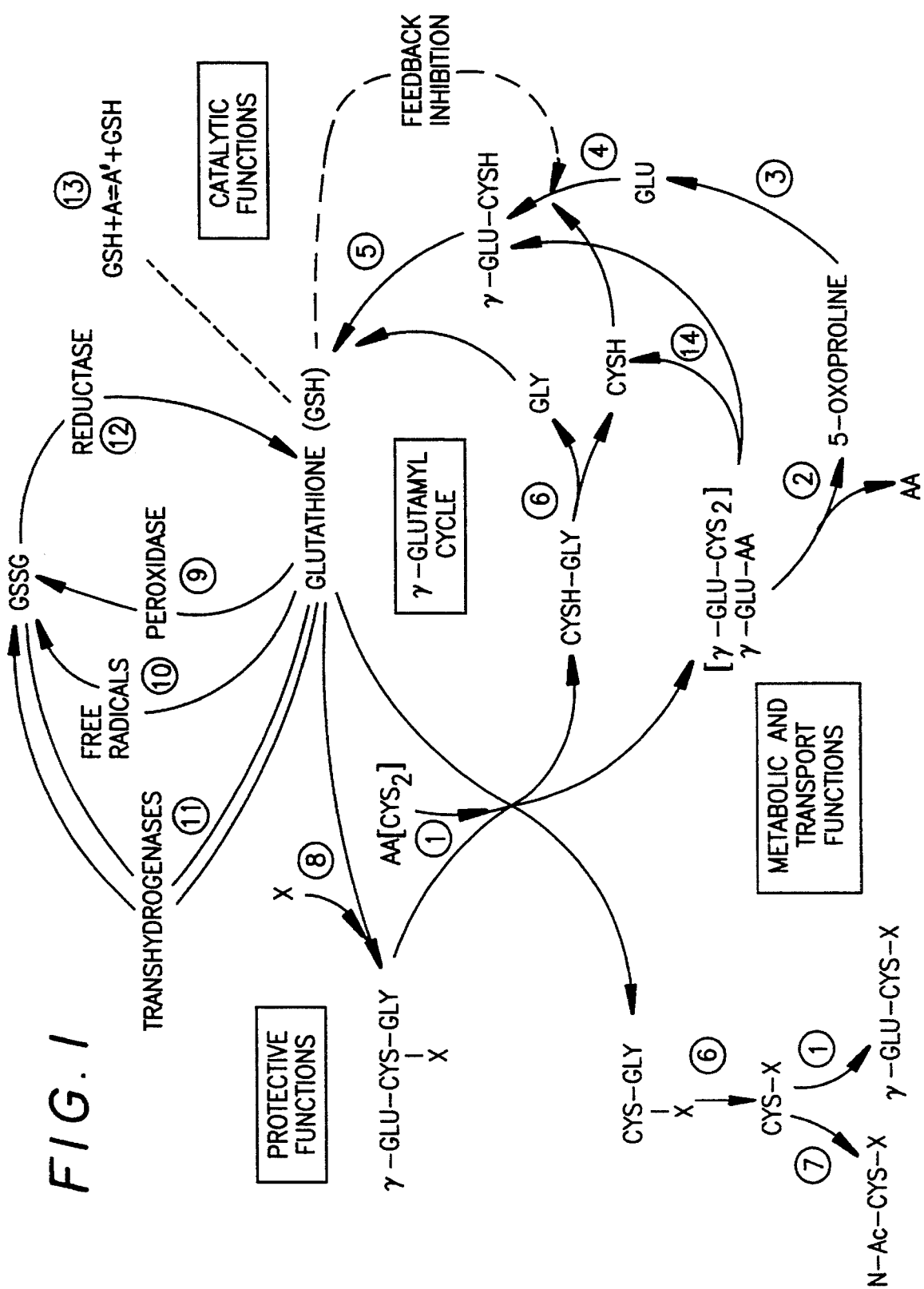
FIG. 1 is an overview of the metabolism and function of glutathione: (1) γ-Glutamyl transpeptidase; (2) γ-glutamyl cyclotransferase; (3) 5-oxoprolinase; (4) γ-glutamylcysteine synthetase; (5) glutathione synthetase; (6) dipeptidase; (7) L-cysteine-S-conjugate N-acetyl transferase; (8) glutathione S-transferase; (9) glutathione peroxidase; (10) presumably nonenzymatic; (11) glutathione transhydrogenases, e.g., enzymes that catalyze thio-protein reactions; (12) glutathione disulfide reductase; (13) reactions in which glutathione is required, but not consumed, such as those catalyzed by formaldehyde dehydrogenase, glyoxylase, maleylacetoacetate isomerase, DDT-dehydrochlorinase, and prostaglandin endoperoxidase isomerases; (14) transport and reduction of γ-glutamylcysteine. AA=amino acids; X=compounds that form conjugates with glutathione. [Thioredoxin and Glutaredoxin Systems: Structure and Function, edited by Al. Holmgren et al, page 340. Raven Press, New York, 1986.]

This invention relates to certain S-substituted homocysteine sulfoximines and their uses. As described above, buthionine sulfoximine (BSO) appears to have significant uses for chemotherapy and radio therapy, especially combination chemotherapy and radiation therapy and for treatment of subjects with parasitic infections. The compounds of the invention have the same above-mentioned utilities as BSO but have one or more superior attributes when compared to BSO.

The compounds of the invention include compounds of the formula:

$$R_4OOCCR_1NH_2CH_2CH_2-\overset{O}{\underset{NH}{\overset{\|}{S}}}-R_2$$

where $R_1$ is H or $-CH_3$ and $R_2$ is alkyl having a 3 to 7 carbon atom backbone and having one or two methyl or one ethyl substitution on said backbone in other than the 1 position, preferably in either the 2 or 3 position (most preferably the 3 position) on the alkyl chain, (i.e. where $R_2$ 2-methyl, 2,2-dimethyl propyl; 2-methyl, 3-methyl, or 2-ethyl butyl; or alkyl having 5 to 7 carbon atoms in its backbone and having one or two methyl or one ethyl groups on said backbone in either the 2 or 3 position), or $-CH_2(CH_2)_x-R_3$ where x is 0 or 1 and $R_3$ is cyclohexyl or phenyl, preferably cyclohexyl and where $R_4$ is H or lower alkyl, preferably, ethyl propyl or isopropyl; most preferably $R_4$ is H. Examples of such compounds include compounds where $R_1$ is H and $R_2$ is $-CH_2CH_2CHCH_3CH_3$, i.e. S-(3-methyl)butyl homocysteine-SR-sulfoximine; $R_2$ is,

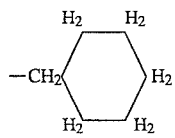

i.e. S(cyclohexyl)methyl homocysteine-SR-sulfoximine; $R_2$ is $-CH_2CH_2C(CH_3)_3$, i.e. S-(3,3-dimethyl)butyl homocysteine-SR-sulfoximine; $R_2$ is $-CH_2CH(CH_2CH_3)CH_2CH_3$ i.e. S-(2-ethyl)butyl homocysteine-SR-sulfoximine; $R_2$ is $-CH_2CH(CH_3)CH_2CH_3$ i.e. S-(2-methyl)butyl homocysteine-SR-sulfoximine; $R_2$ is $-CH_2C(CH_3)_3$ i.e. the equivalent compounds where $R_1$ is methyl, for example S-(methylcyclohexyl)α-methylhomocysteine-SR-sulfoximine and S-(3-methyl)butyl α-methylhomocysteine-SR-sulfoximine; as well as S(2,2-dimethyl)propyl homocysteine-SR-sulfoximine; and $R_2$ is $-CH_2CH(CH_3)_2$ i.e. S-(2-methyl)propyl homocysteine-SR-sulfoximine; as well as compounds where $R_4$ is lower alkyl for example the isopropyl ester of S-(3-methyl)butyl homocysteine-SR-sulfoximine and the ethyl ester of S-(methylcyclohexyl) homocysteine-SR-sulfoximine. Pharmacologically acceptable salts of the compounds of the inventor can also be employed. The DL- and L-analogs are effective. Although the SR pairs have not been resolved, previous work has shown that the S isomer is effective for methionine sulfoximine. The presently preferred compounds are the compounds where $R_1$ is H and $R_2$ is methylcyclohexyl or (3-methylbutyl).

As stated above, where compared to BSO, the compounds of the invention has significant unexpected advantages. It is known that strong inhibition of glutamine synthetase in mice leads to convulsions. As shown in Table 2, the compounds of the invention specifically inhibit γ-glutamylcysteine synthetase. The Ki's vary from about 0.5 to over 50 μM. 3 m BSO and CHMSO were the best inhibitors, about equal to BSO. The compounds of the invention inhibit glutamine synthetase less than BSO, they are more specific for the depletion of glutathione and thus appear to be less toxic.

In addition, varying with the S-hydrocarbyl group, the compounds of the invention display varying tissue distribution, apparently based on differential transport.

Further, it appears the metabolism of the compounds of the invention differ from buthionine sulfoximine. While no BSO was detected in mouse bile, CHMSO was detected in mouse bile. The presence of CHMSO in bile is expected to cause more effect on depletion of glutathione in the intestinal tract than BSO.

The differential rate of uptake and export of these compounds is useful for reducing undesirable depletion of glutathione in some tissues (e.g. the kidney) and/or causing higher depletion in a target tissue, for example 3 m BSO (for example after 2 hr) is more effective than BSO in depleting liver glutathione levels.

Importantly, the compounds of the invention are not transported across the blood-brain barrier, thus they are safer to use, especially repeatedly, than BSO. For example, buthionine sulfoximine (2 mmol/kg;12 hours) decreases brain glutathione levels by almost 20%, while the same dose of CHMSO showed no decrease in brain glutathione levels (with experimental error of about 5%).

It is noted that cardio-toxicity of compounds of the invention appear to be lower than that of BSO. For example 2 hours after the administration of buthionine sulfoximine (2 mmol/kg) to mice, glutathione levels decreased 22%, while after treatment with CHMO, glutathione levels decreased only 8%.

The compounds of the invention can be administered to the patient (animal or human) in an amount effective to accomplish the desired effect, e.g. a cancer chemotherapy or combined cancer chemotherapy/radiation therapy enhancing amount, a parasitic infection treatment enhancing amount, a glutathione depletion causing amount, etc. Typically such an effective amount is an amount between about 0.1 up to about 75 mmoles/kg or more. More typically a dose amount would be between about 0.5 and about 5 mmoles/kg. Presently doses of about 2 mmoles/kg are usually sufficient. The dose can be determined in accordance to the Ki and transport rate for the particular compound. [It is noted that $K_{iapp}$ (apparent inhibition constant) is calculated from a plot of inhibitor concentration against rate.]

The mode of administration of the compounds of the invention can vary widely and is not critical. The compounds, preferably formulated in a pharmaceutically acceptable carrier, for example can be administered orally, subcutaneously, intraperitonically, or intravenously, or even by means of a suppository. The use of implants, including site implants or site delivery means are also contemplated. Where the compound has limited solubility, low pH formulations, given orally, are preferred to enhance solubility.

The methods of the inventions include a method of depleting glutathione levels in cells (in vivo or in vitro) which comprises administering to said cells (including a subject containing said cells) a glutathione depleting amount of a compound of the invention.

Also contemplated is a method for enhancing the effect of chemotherapy (e.g. cancer chemotherapy) on a subject where tissue glutathione levels have an effect on the success of the treatment which comprises administering conjointly a said subject in conjunction with said chemotherapy, a chemotherapy enhancing amount of a compound of the invention.

Also contemplated is a method for enhancing the effect of cancer radiotherapy of a subject which comprises administering conjointly to said subject, prior to said radiotherapy, a radiotherapy enhancing amount of a compound of the invention.

Also contemplated is a method of enhancing the effect of a drug or therapy which acts on a catalase deficient cells which comprises administering conjointly with that drug a cellular peroxidase inhibiting amount of a compound of the invention.

As used herein "conjointly" means at a time and in an amount such that the desired cellular effect contributed by the compounds of the invention is in existence or comes into existence when the primary treatment effect is taking place.

EXAMPLES

Rat kidney γ-Glutamylcysteine synthetase was purified from Sprague Dawley (Taconic Farms) rats (Seelig., *Methods in Enzymology*, 1985, 113:379–390). Glutamine synthetase from sheep brain was from Sigma Chemicals was microdialyzed (Amicon) against imidazole buffer (10 mM,pH 7.2) containing EDTA (1 mM) and DTT is (5 mm).

1-Bromo-3-methylbutane, 1-bromo-2-methylbutane, 1-bromo- 2-methylpropane, bromomethylcyclopropane, 1-bromo-2-ethylbutane, bromomethylcyclohexane and DL-homocysteine thiolactone HCl were from Aldrich Chemicals. L-α-aminobutyric acid was obtained from Vega Biochemicals. L-Methionine, L-methionine-SR-sulfoximine, ATP, phosphoenolpyruvate, NADH, NADPH, lactate dehydrogenase and pyruvate kinase were obtained from Sigma Chemicals. Male Swiss Webster mice (20–25 g) were obtained from Taconic Farms.

DL-alkyl sulfides were synthesized from the appropriate bromo or chlorohydrocarbon and DL-homocysteine thiolactone. L-alkylsulfides were synthesized from the appropriate bromoalkane and L-methionine via sodium and liquid ammonia. The alkyl sulfoximines were synthesized from the sulfides as previously described [see Hope et al, *J. Chem. Soc.(c)*, 270–273 (1970); Griffith et al, *J. Biological Chem.*, (1979), 254:7558–60 and Bentley et al, *J. Proc. Royal Soc. London (B)*, (1951), 138:265–72].

The details of the preparation of DL-3-methyl buthionine are given below. All solutions are bubbled with nitrogen for 15 minutes prior to use. Sodium methoxide (117 mmol) is added carefully to dry methanol (final volume, 210 ml) at 0° C., followed the addition of DL-homocysteine thiolactone HCl (50 mmol). 1-Bromo-3-methylbutane (50 mmol) is added dropwise over 5 minutes. the reaction is stirred for 90 minutes. The solution is filtered and the filtrate is reduced to 20 mls by rotary evaporation. sodium hydroxide (300 mls, 1M) is added and the reaction is refluxed for 3 hours. After cooling to room temperature, the volume then is reduced to 40 mls by rotary evaporation. The solution is cooled to 0° C. and the pH is adjusted to 5 by the slow addition of concentrated HCl. The solution is cooled for 16 hours, and the precipitate is collected by filtration under reduced pressure. The precipitate is dissolved in hot water and refiltered. The product is obtained by recrystallization from hot ethanol.

The synthesis of L-3-methyl buthionine is given below. L-Methionine (100 mmol) is added to a 3-neck flask in a Dry-Ice/acetone bath equipped with an oil seal stirrer and a Dry-Ice/acetone condenser. Liquid ammonia (20 mol) is condensed into the flask. The flask is removed from the Dry-Ice/acetone bath and sodium (280 mmol) is carefully added in small portions (≈0.25 gm) over 90 minutes with stirring; a deep blue color should remain for 30 minutes. After 30 minutes NH$_4$Cl (a few mg) is added to remove the excess sodamide (Caution: a vigorous reaction occurs!) and give a colorless solution. 1-Bromo-3-methylbutane (120 mmol) is added dropwise over 20 minutes. The reaction mixture is allowed to stir for 1 hour. The condenser and stirrer are removed and the ammonia is allowed to evaporate overnight. The white residue is dissolved in 250 ml of water and filtered under reduced pressure. The volume of the filtrate is brought to 500 ml with water and the pH adjusted to 7 with HCl (concentrated). The flask is placed at 4° C. for 16 hours. The precipate is collected by filtration at reduced pressure and washed with cold water, cold ethanol, ether and dried under vacuum over P$_2$O$_5$.

The synthesis of L-(3-methyl)butylbuthionine-SR-sulfoximine (L-(S-3-methylbutyl homocysteine-SR-sulfoximine) is given below. Chloroform (90 ml, dry) and sulfuric acid (25.5 ml, freshly opened) are placed in a 3-neck flask equipped with an oil seal stirrer, a water cooled condenser fitted with a drying tube, and a Teflon stopper. L-(3-methyl)butylbuthionine (45 mmol) is added and the reaction mixture is placed in an oil bath at 46° C. Sodium azide (210 mmol) is added in small portions (every 15 minutes) over 4 hours. Caution: sodium azide and the gaseous hydrazoic acid produced are toxic! The reaction mixture is allowed to cool for 16 hours with stirring for 4 hours. The reaction mixture is extracted three times with water (total volume is 500 ml). The aqueous layer is slowly applied to a Dowex 50(H$^+$) column (5×30 cm). The column is washed with ten volumes of water and eluted first with NH$_4$OH (1M, 2l) and then with 2M NH$_4$OH (2l). The NH$_4$OH eluant is dried by rotary evaporation. The product is crystallized from hot water.

The preincubation assay of γ-glutamylcysteine synthetase is given below. γ-Glutamylcysteine synthetase (4.6 units) was added to a mixture (final volume, 50 μl) containing 100 mM Tris/HCl (pH 8.2), 5 mM ATP, 20 mM $MgCl_2$, 0.2 mM EDTA, and the sulfoximine being evaluated. After incubation at 22° C. for 30 minutes, a 45 μl aliquot of the preincubation mixture was added to the assay as follows.

γ-Glutamylcysteine synthetase was assayed as follows (Griffith et al, *J. Biological Chem.*, 1979, 254:1205–1210). The reaction mixture (final volume, 1.0 ml) contained 100 mM Tris/HCl (pH 8.2), 120 mM KCl, 5 mM phosphoenolpyruvate, 20 mM $MgCl_2$, 10 mM sodium L-glutamate, 10 mM L-α-aminobutyric acid, 0.2 mM EDTA, 0.4 mM NADH, pyruvate kinase (10 IU), and lactate dehydrogenase (10 IU). The reaction (37° C.) was initiated by the addition of γ-glutamylcysteine synthetase and the oxidation of NADH, equivalent to ADP formation, was recorded at 340 nm.

The preincubation assay of glutamine synthetase is given below. Glutamine synthetase (1.3 unit) was added to a mixture (final volume, 50 μl) containing 50 mM imidazole/HCl (pH 7.2), 5 mM ATP, 20 mM $MgCl_2$, and the sulfoximine being evaluated. After incubation at 22° C. for 30 minutes, a 45 μl aliquot of the preincubation mixture was assayed as follows:

Glutamine synthetase was assayed at 37° C. The reaction mixtures (final volume, 1.0 ml) contained 100 mM imidazole/HCl (pH 7.2), 100 mM KCl, 5 mM $NH_4ATP$, 5 mM phosphoenolpyruvate, 20 mM $MgCl_2$, 10 mM $NH_4^+$ L-glutamate, 0.4 mM NADH, pyruvate kinase (10 IU), and lactate dehydrogenase (10 IU). The reaction was initiated by addition of glutamine synthetase.

Male mice (Swiss Webster) were fasted overnight (about 16 hr). L-3-methylbuthionine-SR-sulfoximine (3 mBSO; L-S-3-methylbutyl homocysteine-SR-sulfoximine), L-S-isopentyl homocysteine-SR-sulfoximine, L-buthionine-SR-sulfoximine(BSO; L-S-butyl homocysteine-SR-sulfoximine), L-2-methylbuthiomine-SR-sulfoximine (2 mBSO, L-S-2methylbutyl homocysteine-SR-sulfoximine), or saline (0.9% NaCl) were administered to mice at 2 mmol/Kg intraperitoneally (50 mM, Ph ~7). At the times indicated, plasma and tissues were obtained and assayed for glutathione (GSH+½ GSSG) as described by Anderson, *Methods in Enzymology*, 1985, 113:548–555. (See Table 3.)

Male mice (Swiss Webster) were fasted overnight (about 16 hr.) L-buthionine-SR-sulfoximine (BSO, S-n-butyl homocysteine-SR-sulfoximine), L-S-cyclohexylmethyl homocysteine-SR-sulfoximine (CHMSO); L-S-2-ethylbutyl homocysteine-SR-sulfoximine (2 EtBSO, L-S-2-ethylbutyl homocysteine-SR-sulfoximine, or saline (0.9% NaCl) were administered to mice at 2 mmol/Kg by intubation (100 mM; pH about 1 with HCl (200 mM). At the times indicated, plasma and tissues were obtained and assayed for glutathione (GSH+½ GSSG) as described by Anderson, *Methods in Enzymology*, 1985, 113:548–555. (See Table 4 and 5.)

TABLE 1

| | |
|---|---|
| Inhibition of Glutamine Synthetase | |
| Compound | $K_{iapp}$ Concentration ofr 50% Inhibition |
| L-Methionine-SR-sulfoximine (MSO) | 50 μM |

TABLE 1-continued

| | |
|---|---|
| Inhibition of Glutamine Synthetase | |
| Compound | $K_{iapp}$ Concentration ofr 50% Inhibition |
| L-Buthionine-SR-sulfoximine (BSO) | 21 mM |

Notes:
$K_{iapp}$ could not be determined for L-2-methylbutyl homocysteine-SR-sulfoximine (2m BSO; no inhibition at 32 mm), L-cyclohexylmethyl homocysteine-SR-sulfoximine (CHMSO; no inhibition at 20 mm); 2-ethylbutyl homocysteine-SR-sulfoximine (2ETBSO; no inhibition at 4 mm), or 3-methylbutyl homocysteine-SR-sulfoximine (3m BSO; no inhibition at 20 mM, 7% inhibition at 40 mM).

TABLE 2

| | |
|---|---|
| $K_{iapp}$ for Inhibition of γ-Glutamylcysteine Synthetase | |
| Compound | $K_{iapp}$ (μM); Concentration for 50% Inhibition |
| L-S-n-butyl homocysteine sulfoximine (L-buthionine sulfoximine; BSO) | 0.6 |
| L-S-(3-methyl) butyl homocysteine sulfoximine (L-3-methyl buthionine sulfoximine; 3m BSO) | 0.6 |
| L-S-(2-methyl) butyl homocysteine sulfoximine (L-2-methyl buthionine sulfoximine; 2m BSO) | 18.4 |
| L-S-(2-ethyl) butyl homocysteine sulfoximine (L-2-ethyl buthionine sulfoximine; 2ETBSO) | 43.3 |
| L-S-cyclohexylmethyl homocysteine sulfoximine (CHMSO) | 3.8 |

TABLE 3

Tissue Glutathione Levels After Intraperitoneal Administration of Sulfoximines Glutathione Levels

| Tissue | Treatment | 2 hr μmol/g | 2 hr % Decrease | 12 hr μmol/g | 12 hr % Decrease |
|---|---|---|---|---|---|
| Kidney | Control | 3.74 | 0 | 3.57 | 0 |
| | BSO | 0.76 | 82 | 0.75 | 79 |
| | 3m BSO | 0.73 | 81 | 1.69 | 53 |
| | 2m BSO | 2.08 | 25 | 4.10 | 0 |
| Liver | Control | 5.45 | 0 | 4.98 | 0 |
| | BSO | 1.50 | 72 | 3.37 | 32 |
| | 3m BSO | 1.26 | 77 | 3.86 | 22 |
| | 2m BSO | 4.49 | 18 | 5.05 | 0 |
| Heart | Control | 1.34 | 0 | 1.29 | 0 |
| | BSO | 1.16 | 14 | 0.56 | 57 |
| | 3m BSO | 1.13 | 16 | 0.55 | 57 |
| | 2m BSO | 1.15 | 14 | 1.19 | 8 |
| Brain | Control | 2.31 | 0 | 2.13 | 0 |
| | BSO | 2.08 | 10 | 1.93 | 17 |
| | 3m BSO | 2.09 | 10 | 1.92 | 10 |
| | 2m BSO | 2.19 | 5 | 2.18 | 0 |
| Plasma μM | Control | 29.5 | 0 | 28.7 | 0 |
| | BSO | 10.1 | 66 | 16.3 | 43 |
| | 3m BSO | 10.6 | 64 | 19.2 | 30 |
| | 2m BSO | 25.2 | 15 | 26.3 | 8 |

TABLE 4

Tissue Glutathione After Oral Administration of Sulfoximines

| Tissue | Treatment | 2 hr | | 12 hr | |
|---|---|---|---|---|---|
| | | μmol/g | % Decrease | μmol/g | % Decrease |
| Kidney | Control | 3.47 | 0 | 3.47 | 0 |
| | BSO | 0.69 | 80 | 0.45 | 87 |
| | 2ETBSO | 2.13 | 39 | 3.60 | 0 |
| Liver | Control | 4.98 | 0 | 4.98 | 0 |
| | BSO | 1.23 | 75 | 1.10 | 78 |
| | 2ETBSO | 4.98 | 0 | 4.91 | 1 |
| Brain | Control | 2.10 | 0 | 2.10 | 0 |
| | BSO | 1.86 | 24 | 1.73 | 18 |
| | 2ETBSO | 1.99 | 5 | 2.12 | 0 |
| Plasma | Control | 23.4 | 0 | 23.4 | 0 |
| μM | BSO | 9.7 | 59 | 7.2 | 69 |
| | 2ETBSO | 27.2 | 0 | 25.1 | 0 |

TABLE 5

Tissue Glutathione After Oral Administration of Sulfoximines Glutathione; μmol/g and (% Decrease)

| Tissue | Treatment | 2 hr | | 4 hr | | 8 hr | | 12 hr | |
|---|---|---|---|---|---|---|---|---|---|
| | | μmol/g | % Dec. | μmol/g | % Dec. | μmol/g | % Dec. | μmol/g | % Dec. |
| Kidney | Control | 2.80 | 0 | 2.80 | 0 | 3.07 | 0 | 3.22 | 0 |
| | BSO | 0.81 | 71 | 0.57 | 80 | 0.44 | 86 | 0.30 | 91 |
| | CHMSO | 1.03 | 63 | 1.05 | 63 | 2.52 | 18 | 3.14 | 3 |
| Liver | Control | 5.19 | 0 | 5.19 | 0 | 5.46 | 0 | 4.83 | 0 |
| | BSO | 1.50 | 71 | 0.70 | 87 | 0.60 | 89 | 0.73 | 85 |
| | CHMSO | 2.83 | 46 | 2.57 | 50 | 4.12 | 26 | 4.41 | 9 |
| Heart | Control | 1.10 | 0 | 1.10 | 0 | 1.02 | 0 | 1.15 | 0 |
| | BSO | 0.86 | 22 | 0.91 | 17 | 0.65 | 36 | 0.58 | 49 |
| | CHMSO | 1.01 | 8 | 1.04 | 5 | 0.97 | 5 | 0.82 | 28 |
| Brain | Control | 2.14 | 0 | 2.14 | 0 | 2.31 | 0 | 1.99 | 0 |
| | BSO | 2.17 | 0 | 1.95 | 10 | 2.04 | 12 | 1.64 | 18 |
| | CHMSO | 2.22 | 0 | 2.04 | 6 | 2.23 | 3 | 2.03 | 0 |
| Plasma | Control | 22.2 | 0 | 22.2 | 0 | 22.8 | 0 | 23.7 | 0 |
| μM | BSO | 9.8 | 56 | 7.1 | 68 | 5.1 | 78 | 5.5 | 77 |
| | CHMSO | 16.9 | 24 | 15.3 | 32 | 19.0 | 17 | 21.4 | 10 |

What is claimed is:
1. S-(3-methyl)butyl homocysteine-SR-sulfoximine.
2. S-(cyclohexyl)methyl homocysteine-SR-sulfoximine.

* * * * *